United States Patent [19]
Dahl et al.

[11] Patent Number: 5,782,898
[45] Date of Patent: Jul. 21, 1998

[54] SYSTEM FOR ANCHORING MID-LEAD ELECTRODE ON AN ENDOCARDIAL CATHETER LEAD

[75] Inventors: Roger Dahl, Andover; Duane Zytkovicz, Onamia, both of Minn.

[73] Assignee: Angeion Corporation, Plymouth, Minn.

[21] Appl. No.: 729,900

[22] Filed: Oct. 15, 1996

[51] Int. Cl.⁶ ........................................ A61N 1/05
[52] U.S. Cl. ................... 607/119; 607/122; 607/123; 607/126; 600/374; 600/375
[58] Field of Search .................. 607/119, 122, 607/123, 126, 127, 128, 130; 128/642; 600/373–375

[56] References Cited

U.S. PATENT DOCUMENTS

| | | |
|---|---|---|
| 4,154,247 | 5/1979 | O'Neill. |
| 4,374,527 | 2/1983 | Iversen. |
| 4,401,125 | 8/1983 | Reenstierna. |
| 4,407,303 | 10/1983 | Akerstrom. |
| 4,465,079 | 8/1984 | Dickhudt. |
| 4,497,326 | 2/1985 | Curry. |
| 4,573,480 | 3/1986 | Hirschberg. |
| 4,585,004 | 4/1986 | Brownlee. |
| 4,627,439 | 12/1986 | Harris. |
| 4,892,102 | 1/1990 | Astrinsky. |
| 4,917,115 | 4/1990 | Flammang et al.. |
| 4,962,767 | 10/1990 | Brownlee. |
| 5,127,403 | 7/1992 | Brownlee. |
| 5,172,694 | 12/1992 | Flammang et al.. |
| 5,190,052 | 3/1993 | Schroeppel. |
| 5,571,163 | 11/1996 | Helland. |

*Primary Examiner*—John P. Lacyk
*Assistant Examiner*—David M. Ruddy
*Attorney, Agent, or Firm*—Brad Pedersen

[57] ABSTRACT

A system for passively anchoring mid-lead electrodes on an endocardial catheter lead includes at least one fibrosis-anchoring opening positioned along the exterior surface of the catheter lead body proximal or distal to the mid-lead electrodes for passively securing the catheter lead against the interior wall of the heart. Within the fibrosis-anchoring openings a suitable material is provided for anchoring the catheter lead body to the heart wall by fibrosis. Preferably, the fibrosis-anchoring openings comprise at least a pair of openings positioned only partially around the exterior of the catheter lead body at locations both proximal and distal to the mid-lead electrodes, with the catheter lead body between the fibrosis-anchoring openings being pre-formed to bias the mid-lead electrodes against the heart wall.

13 Claims, 2 Drawing Sheets

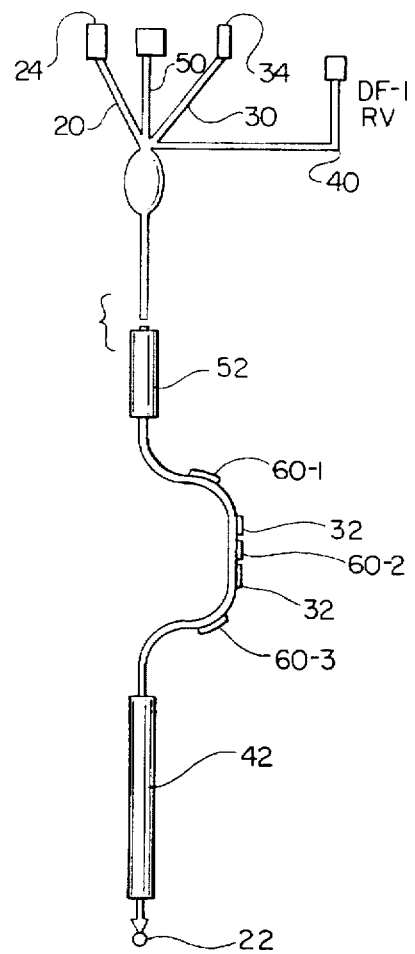
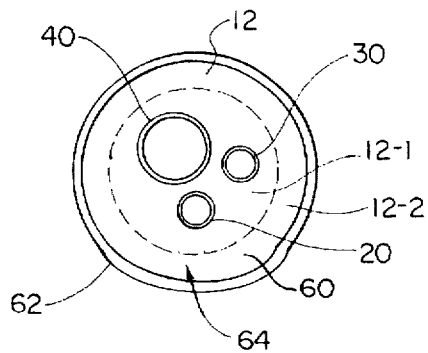
Fig.2
Fig.3
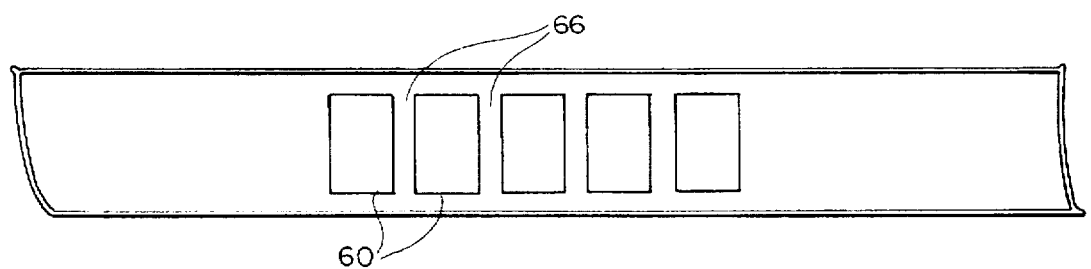
Fig.4
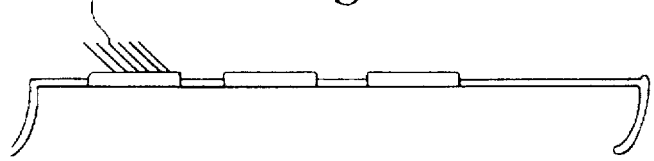
Fig.5

SYSTEM FOR ANCHORING MID-LEAD ELECTRODE ON AN ENDOCARDIAL CATHETER LEAD

FIELD OF THE INVENTION

The present invention relates to transvenous catheter leads for use with pacemakers and defibrillators. More particularly, the present invention relates to a system for passively anchoring a mid-lead electrode, such as for pacing/sensing the atrium, on a an endocardial catheter lead.

BACKGROUND OF THE INVENTION

In treating cardiac arrhythmias, it is well known that the ability to sense electrical activity in both chambers of the heart can greatly improve both the range of therapies available, as well as the effectiveness of those therapies. In a typical endocardial pacemaker, a first catheter lead having an electrode at the distal end is positioned to pace and sense the ventricle, and a second catheter lead having an electrode at the distal end is positioned to pace and sense the atrium. In a defibrillator system, a defibrillation electrode is added to one, or both, of the catheter leads to deliver high voltage defibrillation countershocks to the ventricle and/or atrium. While the use of two separate endocardial catheter leads for the ventricle and atrium has certain advantages, primarily in terms of independently optimizing electrode location within each chamber of the heart, the obvious disadvantage of this approach is that it requires two separate catheter leads to be inserted into the heart.

Although the idea of providing a single endocardial catheter lead for treating both the atrium and ventricle has long been known, to date, there has been little success in achieving this objective. Prior attempts to implement a single-pass, endocardial catheter lead can be classified into two categories: (1) distal end electrode configurations, and (2) mid-lead electrode configurations. In the first category, the electrodes for pacing and sensing each chamber of the heart are located on two separate distal end portions of the same catheter lead. While this approach allows for optimum location and attachment of each distal end electrode, it has been found that the separation of the catheter lead into two branches or legs within the heart increases the opportunity for thrombus to develop resulting in the possible sloughing off of emboli, particularly at the point at which the two branches of the catheter lead join together. In the second category, the electrodes for pacing and sensing the ventricle are located on the distal end portion of the catheter lead and the electrodes for pacing and sensing the atrium are located mid-lead along the body of the catheter lead within the atrium. While this approach avoids the thrombus problem of two branch catheter leads, it has been difficult to develop long-term effective pacing and sensing using mid-lead electrodes in the atrium.

Presently, most of the mid-lead electrode endocardial catheter leads which have been commercially released utilize a free-floating approach for positioning the electrodes within the atrium. Examples of this approach are shown in U.S. Pat. Nos. 4,585,004, 4,892,102, 4,917,115, 4,962,767, 5,127,403 and 5,172,694, all of which describe different ways to optimize the positioning of the free-floating electrodes in order to sense the P-wave electrical signals associated with the atrium. While free-floating electrodes can provide good sensing, the lack of constant chronic contact with the wall of the atrium decreases the long-term effectiveness of these electrodes.

Examples of other mid-lead electrode endocardial catheter leads which utilize some form of biasing to press the electrode against the atrial wall are shown in U.S. Pat. Nos. 4,154,247, 4,401,126 and 4,627,439. There are significant challenges, however, in designing a mechanical biasing arrangement that will prove effective over the long-term as the atrial electrodes are subject to movement due to cardiac activity, respiration and patient movement or orientation.

A endocardial catheter lead with mid-lead electrode which utilizes a barbed attachment mechanism and porous electrodes is shown in U.S. Pat. No. 4,497,326. This approach is quite similar to the various techniques known for securing a distal end electrode, such as are shown, for example, in U.S. Pat. Nos. 3,737,579, 4,444,206, 4,620,550, 4,972,849, 5,074,313, 5,330,520 and 5,423,884. All of these patents show some form of active fixation mechanism (e.g., a hook, barb, tine, corkscrew or fin designed to penetrate the heart wall) for the distal end electrode. While this approach would seem to solve the problems of the free-floating approach and the mechanical biasing approach, the tension and stress induced on active fixation mechanisms at the mid-lead electrode by the continual movement of the more securely anchored distal end electrode can potentially cause abrasion or scarring of the atrial wall tissue.

The use of a passive fixation mechanism, instead of an active fixation mechanism, for securing distal end electrodes, is shown in U.S. Pat. Nos. 4,374,527, 4,407,303, 4,573,480 and 4,465,079. In these patents, insulating material which extends from the orientation of the catheter lead proximate the distal end of the catheter lead is utilized to encourage fibrosis so as to anchor the distal end electrode in a manner similar to a distal end active fixation mechanism. All of these patents, however, are limited to single chamber catheter leads having distal end electrodes.

SUMMARY OF THE INVENTION

The present invention provides a system for passively anchoring mid-lead electrodes on an endocardial catheter lead. The system includes at least one fibrosis-anchoring opening positioned along an exterior surface of the catheter lead body proximal or distal to the mid-lead electrodes for passively securing the catheter lead against the interior wall of the heart. The fibrosis-anchoring openings are provided with a suitable material for anchoring the catheter lead body to the heart wall by fibrosis, such as a biocompatible fabric, a polymer mesh, porous film, polyester, polyethylene, polypropolyene or an expanded polytetraflouroethylene material. Preferably, the fibrosis-anchoring openings comprise at least a pair of openings positioned only partially around the exterior of the catheter lead body at locations proximal and/or distal to the mid-lead electrodes, with the catheter lead body between the fibrosis-anchoring openings being pre-formed to bias the mid-lead electrodes against the heart wall.

By anchoring the endocardial catheter lead to the atrial wall at a location other than the mid-lead electrodes, the present invention overcomes the disadvantages of the existing endocardial catheter leads by isolating the mid-lead electrodes from movement induced elsewhere along the catheter lead body without the use of an active fixation mechanism. As a result, the interface between the mid-lead electrodes and the heart wall is more constant and stable, and can be optimized for sensing and pacing without concern about utilizing the mid-lead electrode surface to minimize electrode movement.

BRIEF DESCRIPTION OF THE DRAWINGS

FIG. 2 is a top plan view of a preferred embodiment of an endocardial catheter lead.

FIG. 3 is a detailed cross-sectional view of FIG. 2 along lines 3—3.

FIG. 4 is a detailed plan view of FIG. 2 showing the fibrosis-anchoring window.

FIG. 5 is a detailed plan view of an alternate embodiment of the present invention.

DETAILED DESCRIPTION OF THE PREFERRED EMBODIMENT

Figure 1:
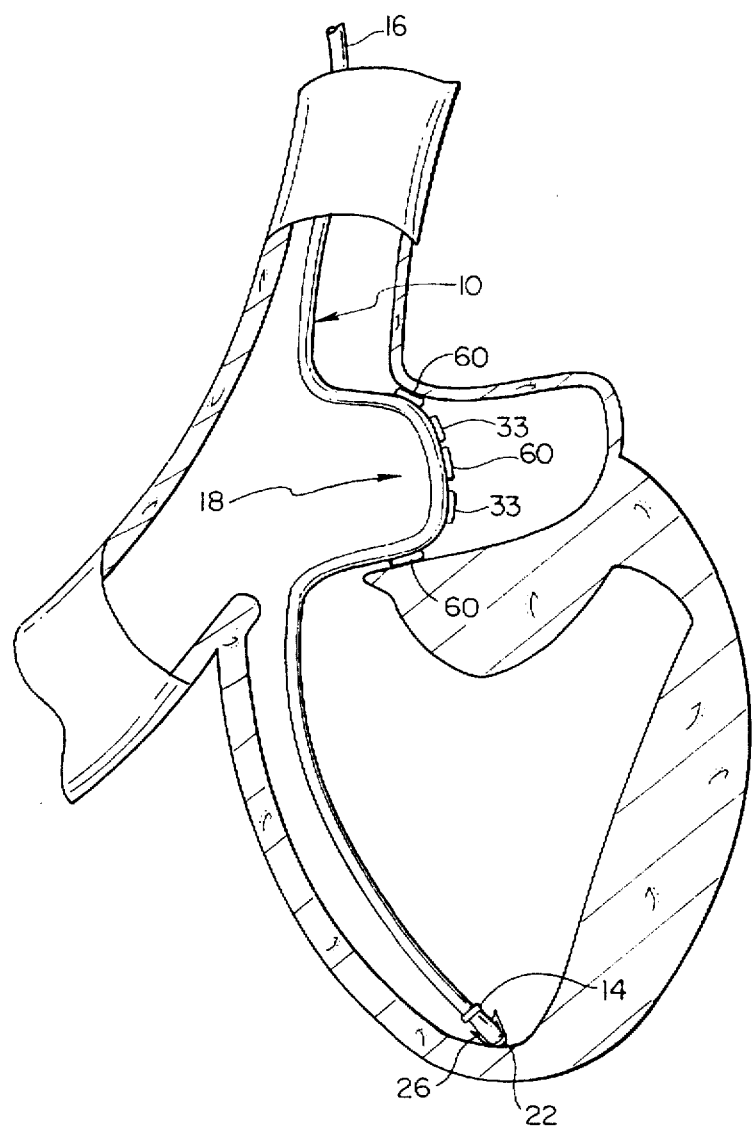
FIG. 1 is a schematic representation showing a preferred embodiment of the present invention in position in a heart.

Referring to FIG. 1, a schematic representation of an endocardial catheter lead 10 in accordance with the present invention is shown in position in a human heart. As shown in FIG. 2, catheter lead 10 includes at least two conductors 20, 30 disposed within an insulative body 12. A first conductor 20 is connected at distal end 14 of catheter lead 10 to a distal end electrode 22 and at proximal end 16 of catheter body 10 to a connector 24. Tines 26 or other passive or active fixation mechanisms could also be utilized to secure distal end 14 to the heart wall. A second conductor 30 is connected at a mid-lead portion 18 of catheter body 10 to a mid-lead electrode 32 and at proximal end 16 of catheter body 10 to a connector 34. Mid-lead portion 18 is preferably defined so as to be positioned within the atrium of the human heart with distal end 14 positioned in the apex of the right ventricle. Alternatively, mid-lead portion 18 could be defined so as to be within the ventricle and distal end 14 could be positioned in the atrium, such as shown in U.S. Pat. No. 5,476,499, or a mid-lead portion 18 could be defined in both the atrium and the ventricle. At a minimum, mid-lead portion 18 is at least 2-3 cm proximal to distal end 14 of catheter body 10. In operation, connectors 24 and 34 are connected to an implantable pulse generator (not shown), such as a pacemaker or defibrillator.

The selection and design of conductors 20, 30 and electrodes 22, 32 is known in the art. Preferably, conductors 20, 30 and electrodes 22, 32 are each comprised of a pair of conductors and electrodes so as to implement bi-polar sensing and/or pacing. Alternatively, conductor 20 and electrode 22 may be singular and a third conductor 40 can be provided to connect to a cardioversion/defibrillation electrode 42 positioned between electrodes 22 and 32, such that electrodes 22 and 42 would provide for integrated bi-polar sensing and pacing in the ventricle. Similarly, conductor 30 and electrode 32 may be singular and a fourth conductor 50 can be provided to connect to a cardioversion/defibrillation electrode 52 positioned proximal or distal to electrode 32 within the atrium or super vena cava, for example, such that electrodes 32 and 52 would provide for integrated bi-polar sensing and pacing in the atrium. In another embodiment, electrode 22 could be a distal defibrillation electrode and electrode 32 could be a pace/sense electrode. In still another embodiment, electrode 32 could be a defibrillation electrode and electrode 22 could be a distal pace/sense electrode.

Catheter body 10 is constructed in a known manner in a multi-lumen or coaxial arrangement, although other longitudinal arrangements of conductors and insulators within catheter body 10 could be utilized as well. Insulative body 12 is preferably comprised of silicone, although other biocompatible insulative materials such as polyurethane could be utilized. In at least one location in mid-lead portion 18, a fibrosis-anchoring opening 60 is provided on at least a portion of the outer surface of insulative body 12. A suitable biocompatible anchor material 62 is positioned within opening 60 for passively anchoring the catheter body 10 to the heart wall by fibrosis. Examples of suitable anchor materials include: a biocompatible fabric, a polymer mesh, porous film, polyester, or polyethylene, polypropolyene or an expanded polytetraflouroethylene material. Ideally, the average mesh opening size of anchor material 62 is between 80 and 400 microns.

As shown in FIG. 3, preferably the silicone behind opening 60 is elevated slightly above the exterior surface of insulative body 12 elsewhere so as to create a small, flattened surface 64 oriented toward the intended interface between opening 60 and the interior heart wall. FIG. 3 also shows how opening 60 extends only partially around the circumference of catheter body 10. By limiting the extent of opening 60 in this manner, and by properly orienting opening 60 to the interior heart wall, the risk of any emboli formed by virtue of the fibrosis of anchor material 62 with the heart wall is minimized.

In a preferred embodiment as shown in FIG. 2, mid-portion 18 of catheter lead 10 is curved to urge electrodes 32-1 and 32-2 against the inner wall of the auricle of the atrium. Any number of known techniques for pre-shaping catheter lead 10 may be used to accomplish this, such as forming insulative material 12 with a pre-shaped bend, utilizing additional insulative material to build up one side of catheter lead 10 to create a curved section, or utilizing a memory-shaped metal or thermoset plastic to define a curved portion. Preferably, the biasing of mid-portion 18 of catheter lead 10 provides a sufficient lateral force to urge electrodes 32-1 and 32-2 against the vertically oriented inner wall of the auricle of the atrium, for example. Obviously, other curved configurations and biasing combinations would be required if mid-portion 18 were adapted to abut against other locations with the heart, such as the posterior lateral wall of the atrium, the orifice of the SVC or the ventricular apex.

In the configuration shown in FIG. 2, three openings 60-1, 60-2 and 60-3 are used to secure mid-portion 18 to the atrial wall, thereby isolating electrodes 32-1 and 32-2 from motion induced elsewhere on catheter lead 10. The top opening 60-1 is preferably located above and proximal a top horizontal segment of mid-portion 18 so as to isolate electrodes 32-1 and 32-2 from any motion in the proximal portion of catheter lead 10, such as lateral motion induced by respiratory or body movement. The bottom opening 60-3 is preferably located along a bottom horizontal segment of mid-portion 18 so as to isolate electrode 32-1 and 32-2 from any motion in the distal portion of catheter lead 10, such a vertical motion induced in electrode 22 by ventricular contractions. At a minimum, bottom opening 60-3 is located no closer than 2 cm to distal end 14, and preferably is located at least 5 cm from distal end 14. Middle opening 60-2 is optionally positioned between the two electrodes 32-1 and 32-2 so as to secure mid-portion 18 to the interior surface of the atrial wall, thereby aiding electrodes 32-1 and 32-2 to remain in contact with the atrial wall as the atrial wall moves during contractions of the heart. Because the movement of the atrial wall is relatively small, as compared to the movement in the ventricle wall, for example, the function of opening 60-2 may be accomplished by other mechanisms, such as biasing of mid-portion 18 toward the atrial wall, fibrosis of electrodes 32-1 and 32-2 to the atrial wall, or even use of an active fixation mechanism which, due to the use of openings 60-1 and 60-3, would have much less chance of abrasion and scarring of the atrial wall due to movement elsewhere in catheter lead 1 0.

While the preferred embodiment utilizes openings 60 to accomplish stabilization and isolation of atrial electrodes 32, it will be recognized that it is possible to utilize the present invention in combination with other stabilization techniques. For example, upper opening 60-1 might be replaced with structure, such as the spiral loops in the superior vena cava as taught by U.S. Pat. No. 4,394,866. Alternatively, one or both of openings 60-1 or 60-3 might be replaced or augmented by loops in either the atrium or techniques in either the atrium or ventricle, respectively, as taught, for example, by U.S. Pat. Nos.4,154,247, 4,401,126, 4,627,439 and 5,405,374. It is also possible to use a surgical adhesive, such as is disclosed in U.S. Pat. No. 4,768,523, or other similar temporary attachment techniques to temporarily secure the fibrosis-anchoring openings 60 to the heart wall until fibrosis occurs.

Referring to FIGS. 3 and 4, the preferred construction of opening 60 and anchor material 62 are described in more detail. As shown in FIG. 3, insulative material 12 is preferably comprised of a pair of extruded silicone tubes, an inner tube 12-1 which contains a coaxial conductor 40 and a pair of drawn braised strand (DBS) conductors 20 and 30, and an outer tube 12-2 into the exterior of which openings 60 are constructed. The outer tube 12-2 is a premolded piece that incorporates the flattened, elevated opening 64. As shown in FIG. 4, openings 60 are preferably constructed as a plurality of windows cut or molded into outer tube 12-2 so that some material of porous anchoring material 62, as shown at 66, remains between adjacent openings 60. Anchor material 62 is positioned within openings 60 or may be molded into openings 60. Once anchor material 62 is assembled, outer tube 12-2 is swelled and inner-tube 12-1 is drawn inside to complete the assembly. Medical adhesive, pressure, temperature or any combination thereof may be used to secure inner tube 12-1 to outer tube 12-2.

Referring to FIG. 5, an alternate construction of opening 60 and anchor material 62 are described. In this embodiment, anchor material 62 includes protruding fibers 68 which are allowed to extend outward from opening 60 to further encourage fibrosis so as to anchor catheter lead 10. Fibers 68 are connected to and extend from a base of anchor material 62 located within opening 60. Fibers 68- may be maintained in a longitudinal orientation during implantation of catheter lead 10 by the use of Manital® or a similar dissolvable coating material. By manipulation of a stylet (not shown) during implantation, fibers 68 can be extended beyond opening 60 and may even work their way into the interior cardiac wall.

I claim:

1. An endocardial catheter lead comprising:
   an elongated insulative body member; at least two conductors disposed within the insulative body member, including:
   a first conductor connected at a distal end of the lead body member to a distal end electrode and at a proximal end of the body member to a first connector; and
   a second conductor connected at a mid-lead portion of the body member to a mid-lead electrode and at the proximal end of the body member to a second connector; and at least one fibrosis-anchoring opening defined in an exterior surface of the insulative body member and positioned along the insulative body member proximate the mid-lead electrode and having therein an anchoring material comprising: at least a portion of a sheet having multiple openings defined therein for securing the catheter lead against the interior wall of the heart by fibrosis.

2. The catheter lead of claim 1 wherein the endocardial lead is a endocardial lead and the mid-lead portion is adapted for positioning within the atrium of the heart.

3. The catheter lead of claim 1 comprising a plurality of fibrosis-anchoring openings including a first opening positioned proximal to the mid-lead electrode and a second opening positioned distal to the mid-lead electrode.

4. The catheter lead of claim 3 wherein each fibrosis-anchoring opening includes a plurality of adjacent openings oriented along a longitudinal axis of the body member.

5. The catheter lead of claim 1 wherein the mid-lead electrode includes at least two atrial electrodes spaced apart along the insulative body member for pacing and sensing the atrium in a bi-polar configuration.

6. The catheter lead of claim 5 wherein the fibrosis-anchoring opening is positioned between the two atrial electrodes.

7. The catheter lead of claim 1 wherein the anchoring material is selected from the set consisting of: a biocompatible fabric, a polymer mesh, polyester, porous film, polyethylene, polypropolyene or an expanded polytetraflouroethylene material.

8. The catheter lead of claim 1 further comprising biasing means operative along the mid-lead portion for biasing the mid-lead electrode against the interior wall of the heart.

9. The catheter lead of claim 1 wherein the insulative body member is comprised of an inner tube having a cross-sectional area that is generally coextensive along a longitudinal length of the body member between the proximal end and the distal end of the body member containing the first and second conductors and an outer tube in which the opening is defined.

10. The catheter lead of claim 1 wherein the anchor material is a woven material that include fibers which extend outward beyond the catheter body.

11. An endocardial catheter lead comprising:
    an elongated insulative body member;
    a conductor connected at a mid-lead portion of the catheter body to a mid-lead electrode and at the proximal end of the catheter body to a connector; and at least one fibrosis-anchoring opening defined in an exterior surface of the insulative body member and positioned along the insulative body member proximate the mid-lead electrode and at least 2 cm from a distal end of the catheter body and having positioned therein an anchoring material comprising: at least a portion of a sheet having multiple openings defined therein for securing the catheter lead against the interior wall of the heart by fibrosis.

12. A method of forming an endocardial catheter lead comprising the steps of:
    (a) providing an elongated insulative body member;
    (b) inserting a conductor into the insulative body member and connecting the conductor to a mid-lead electrode at a mid-lead portion of the catheter body and to a connector at the proximal end of the catheter body;
    creating at least one fibrosis anchoring opening defined in an exterior surface of the insulative body member and positioned along the insulative body member proximate the mid-lead electrode and at least 2 cm from a distal end of the catheter body; and
    (d) disposing in the opening an anchoring material comprising: at least a portion of a sheet having multiple openings defined therein for securing the catheter lead against the interior wall of the heart by fibrosis.

13. The method of claim 12 wherein the insulative body member is comprised of an inner tube and an outer tube and wherein the conductor is inserted into the inner tube in step (b) and the opening is created in the outer tube in step (c) and further comprising the step of:
    (e) coaxially assembling the inner tube and the outer tube to form the catheter lead.

* * * * *